(12) United States Patent
Peine

(10) Patent No.: US 11,925,429 B2
(45) Date of Patent: Mar. 12, 2024

(54) REPOSITIONING METHOD OF INPUT DEVICE FOR ROBOTIC SURGICAL SYSTEM

(71) Applicant: Covidien LP, Mansfield, MA (US)

(72) Inventor: William Peine, Ashland, MA (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 17/745,994

(22) Filed: May 17, 2022

(65) Prior Publication Data
US 2022/0273385 A1 Sep. 1, 2022

Related U.S. Application Data

(63) Continuation of application No. 16/546,554, filed on Aug. 21, 2019, now Pat. No. 11,331,158, which is a
(Continued)

(51) Int. Cl.
*A61B 34/00* (2016.01)
*A61B 34/30* (2016.01)
(Continued)

(52) U.S. Cl.
CPC .............. *A61B 34/77* (2016.02); *A61B 34/30* (2016.02); *A61B 34/35* (2016.02); *A61B 34/74* (2016.02);
(Continued)

(58) Field of Classification Search
CPC ......... A61B 34/77; A61B 34/30; A61B 34/35; A61B 34/74; A61B 90/361; A61B 90/37; B25J 13/065
See application file for complete search history.

(56) References Cited

U.S. PATENT DOCUMENTS 6,132,368 A 10/2000 Cooper
6,206,903 B1 3/2001 Ramans
(Continued)

FOREIGN PATENT DOCUMENTS

KR 20120068597 A 6/2012
KR 20130015437 A 2/2013
(Continued)

OTHER PUBLICATIONS

Indian Office Action dated Jul. 6, 2020 corresponding to counterpart Patent Application IN 201717027545.
(Continued)

*Primary Examiner* — Robert T Nguyen
(74) *Attorney, Agent, or Firm* — Carter, DeLuca & Farrell, LLP

(57) ABSTRACT

A robotic surgical system includes a linkage, an input handle, and a processing unit. The linkage moveably supports a surgical tool relative to a base. The input handle is moveable in a plurality of directions. The processing unit is in communication with the input handle and is operatively associated with the linkage to move the surgical tool based on a scaled movement of the input handle. The scaling varies depending on whether the input handle is moved towards a center of a workspace or away from the center of the workspace. The workspace represents a movement range of the input handle.

16 Claims, 5 Drawing Sheets

Related U.S. Application Data continuation of application No. 15/548,439, filed as application No. PCT/US2016/014031 on Jan. 20, 2016, now Pat. No. 10,695,142.

(60) Provisional application No. 62/118,123, filed on Feb. 19, 2015.

(51) Int. Cl.
*A61B 34/35* (2016.01)
*B25J 13/06* (2006.01)
*A61B 90/00* (2016.01)

(52) U.S. Cl.
CPC ........... *B25J 13/065* (2013.01); *A61B 90/361* (2016.02); *A61B 90/37* (2016.02)

(56) References Cited

U.S. PATENT DOCUMENTS

| | | |
|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Piolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |

(56) References Cited

U.S. PATENT DOCUMENTS

| | | |
|---|---|---|
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,649,554 B2 * | 2/2014 | Markovic .............. G06F 3/016 |
| | | 382/103 |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,179,979 B2 * | 11/2015 | Jinno .................... A61B 34/37 |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,155,315 B2 | 12/2018 | Ogawa et al. |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |

(56) References Cited

U.S. PATENT DOCUMENTS

| | | |
|---|---|---|
| 10,575,909 B2 | 3/2020 | Robinson et al. |
| 10,592,529 B2 | 3/2020 | Hoffman et al. |
| 10,595,946 B2 | 3/2020 | Nixon |
| 10,603,127 B2 | 3/2020 | Hasser et al. |
| 10,695,142 B2 | 6/2020 | Peine |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | Mcdonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,331,158 B2 | 5/2022 | Peine |
| 2007/0021738 A1 | 1/2007 | Hasser et al. |
| 2007/0083098 A1* | 4/2007 | Stern ............... A61B 34/35 600/407 |
| 2008/0215065 A1 | 9/2008 | Wang |
| 2010/0332033 A1* | 12/2010 | Diolaiti ............ B25J 9/1689 700/263 |
| 2011/0295268 A1 | 12/2011 | Roelle et al. |
| 2011/0301616 A1 | 12/2011 | Sanchez et al. |
| 2012/0116416 A1 | 5/2012 | Neff et al. |
| 2013/0331644 A1 | 12/2013 | Pandya et al. |
| 2014/0316434 A1* | 10/2014 | Simaan ............ A61B 34/74 606/130 |
| 2015/0025549 A1* | 1/2015 | Kilroy ............. A61B 90/361 606/130 |
| 2020/0289221 A1* | 9/2020 | Denlinger ......... A61B 17/29 |
| 2021/0000558 A1 | 1/2021 | Penny |
| 2021/0038296 A1 | 2/2021 | Sartor |
| 2022/0387128 A1* | 12/2022 | Bail ................ A61B 34/74 |
| 2023/0110248 A1* | 4/2023 | Faraji .............. A61B 34/30 700/254 |
| 2023/0126506 A1* | 4/2023 | Wilson ............ A61B 34/35 606/130 |

FOREIGN PATENT DOCUMENTS

| | | |
|---|---|---|
| KR | 1020130015437 | 2/2013 |
| WO | 2015012241 A1 | 1/2015 |

OTHER PUBLICATIONS

International Search Report dated Apr. 20, 2016, issued in PCT/US2016/014031.
European Search Report dated Oct. 15, 2018 cited in EP 16752764.
Australian Examination Report No. 1 dated Sep. 18, 2019 corresponding to counterpart Patent Application AU 2016220501.
Japanese Office Action dated Sep. 26, 2019, issued in JP Appln. No. 2017542842.
Chinese Third Office Action dated Dec. 4, 2020 corresponding to counterpart Patent Application CN 201680011105.4.
Australian Examination Report No. 3 for Application No. AU 2020201796 dated Aug. 12, 2020.
Australian Examination Report No. 1 dated Jun. 26, 2020 corresponding to counterpart Patent Application AU 2020201796.
Chinese First Office Action dated Oct. 29, 2019 corresponding to counterpart Patent Application CN 201680011105.4.
Japanese Office Action dated Jan. 9, 2020 corresponding to counterpart Patent Application JP 2017-542842.
Australian Examination Report for Application No. 2020201796 dated Jul. 17, 2020.
Chinese Second Office Action dated Jun. 10, 2020 corresponding to counterpart Patent Application CN 201680011105.4.
Chinese Fourth Office Action dated Apr. 27, 2021 corresponding to counterpart Patent Application CN 201680011105.4.
Japanese Office Action dated Mar. 31, 2021 corresponding to counterpart Patent Application JP 2020-083039.
Chinese Decision of Rejection dated Aug. 13, 2021 corresponding to counterpart Patent Application CN 201680011105.4.
Australian Examination Report No. 1 dated Sep. 1, 2021 corresponding to counterpart Patent Application AU 2020227038.
Canadian Office Action dated Sep. 16, 2022 corresponding to counterpart Patent Application CA 2,975,907.
Chinese First Office Action dated May 12, 2023 issued in Application No. CN 2021113610744 (6 pages).

* cited by examiner

REPOSITIONING METHOD OF INPUT DEVICE FOR ROBOTIC SURGICAL SYSTEM

CROSS-REFERENCE TO RELATED APPLICATION

This application is a Continuation application claiming the benefit of and priority to U.S. patent application Ser. No. 16/546,554, filed on Aug. 21, 2019 (now U.S. Pat. No. 11,331,158), which is a Continuation application claiming the benefit of and priority to U.S. patent application Ser. No. 15/548,439, filed on Aug. 3, 2017 (now U.S. Pat. No. 10,695,142), which is a U.S. National Stage Application, filed under 35 U.S.C. § 371(a), of International Patent Application Serial No. PCT/US2016/014031, filed on Jan. 20, 2016, which claims the benefit of and priority to U.S. Provisional Patent Application Ser. No. 62/118,123, filed on Feb. 19, 2015, the entire disclosure of each of which being incorporated by reference herein.

BACKGROUND

Robotic surgical systems have been used in minimally invasive medical procedures. During a medical procedure, the robotic surgical system is controlled by a surgeon interfacing with a user interface. The user interface allows the surgeon to manipulate an end effector that acts on a patient. The user interface includes an input controller or handle that is moveable by the surgeon to control the robotic surgical system.

Robotic surgical systems typically used a scaling factor to scale down the motions of the surgeon's hands to determine the desired position of the end effector within the patient so that the surgeon could more precisely move the end effector inside the patient. However, the larger the scaling factor, the farther the surgeon had to move the input device handle to move the end effector the same distance. Since the input device handle has a fixed range of motion, this meant that for larger scaling factors the surgeon may have reached an end of the range of motion of an input handle more often. The surgeon then had to "clutch" the handle to decouple the motion of the input handles from the end effector so that the surgeon could move the handles to a new position within the workspace of the user interface away from the end of the range motion while the instruments remain stationary. Once the input handle was moved sufficiently away from the end of the range of motion, the surgeon "reclutched" the input handle with the end effector to recouple the motion of the input handle to motion of the end effector to complete the desired movement of the end effector. This clutching process is time consuming and distracting to surgeons.

There is a need for robotic surgical system that is able to scale down input handle movements of the surgeon while also reducing or eliminating the need for a surgeon to clutch or move the input handles away from an end of their range of motion during robotic surgical procedures.

SUMMARY

In an aspect of the present disclosure, a robotic surgical system includes a linkage, an input handle, and a processing unit. The linkage moveably supports a surgical tool relative to a base. The input handle is moveable in a plurality of directions. The processing unit is in communication with the input handle and is operatively associated with the linkage to move the surgical tool based on a scaled movement of the input handle. The scaling varies depending on whether the input handle is moved towards a center of a workspace or away from the center of the workspace. The workspace represents a movement range of the input handle.

In aspects, the processing unit is configured to scale a first movement of the input handle towards the center of the workspace by a first scaling factor and to scale a second movement of the input handle away from the center of the workspace by a second scaling factor different from the first scaling factor.

In some aspects, the processing unit is configured to scale the input distance by dividing a distance of the first movement by the first scaling factor and a distance of the second movement by the second scaling factor. The first and second scaling factors may be in a range of about 1.0 to about 10.0 and the second scaling factor may be larger than the first scaling factor. The first scaling factor may be between 0.70 and 1.40 times as large as the second scaling factor.

In certain aspects, the processing unit is configured to vary the scaling based on a distance of the input handle from the center of the workspace. The processing unit may be configured to linearly or exponentially scale the input distance based on a distance of the input handle from at least one of the center of the workspace and a limit of movement of the input handle. The processing unit may be configured to increase a movement of the surgical tool as the location of the input handle is further from the center of the workspace. The processing unit may be configured to decrease a movement of the surgical tool as the location of the input handle is further from the center of the workspace.

In particular aspects, the workspace includes a first section that is located a predetermined distance from the center of the workspace. The first and second scaling factors may be constant when the input handle is in the first section and at least one of the first or second scaling factors varies when the input handle is outside of the first section.

In another aspect of the present disclosure, a robotic surgical system includes a linkage, an input handle, and a processing unit. The linkage moveably supports a surgical tool relative to a base. The input handle is moveable a first input distance in a first input direction and a second input distance in a second input direction that is opposite the first input direction. The second input distance is different from the first input distance. The processing unit is in communication with the input handle and is operatively associated with the linkage to move the surgical tool. The processing unit is configured to move the surgical tool an output distance in a first output direction in response to the first input distance and to move the surgical tool the same output distance in a second out direction opposite the first input direction in response to the second input distance.

In another aspect of the present disclosure, a method of operating a surgical robot includes detecting a plurality of movements of an input handle that is moveable in a plurality of directions, scaling a detected movement of the input handle towards a center of a workspace by a first scaling factor, scaling a detected movement of the input handle away from the center of the workspace by a second scaling factor different from the first scaling factor, and actuating a linkage based on the scaled detected movements to move a surgical tool that is moveably supported by the linkage.

In aspects, the method includes dividing a distance of the detected movement of the input handle toward the center of the workspace by the first scaling factor and dividing a distance of the detected movement of the input handle away from the center of the workspace by the second scaling factor.

In some aspects, the method includes varying the scaling of the detected movements based on a distance of the input handle from the center of the workspace. The method may include linearly or exponentially varying the scaling of the detected movements based on a distance of the input handle from at least one of the center of the workspace and a limit of movement of the input handle.

In certain aspects, the method may include adjusting the actuation of the linkage to increase or decrease a movement of the surgical tool as the location of the input handle is further from the center of the workspace. The method may include setting the first and second scaling factors as constant when the input handle is in a section of the workspace located within a predetermined distance of the center of the workspace and varying at least one of the first and second scaling factors when the input handle is outside the section.

In another aspect of the present disclosure, a robotic surgical system includes an arm having an end, a tool supported on the end of the arm, an input handle, and a processing unit. The input handle is moveable an input distance and includes a repositioning control that has activated and deactivated states. The processing unit is in communication with the input handle and is operatively associated with the arm to move the tool. The processing unit is configured to scale the input distance of the input handle by a first scaling factor when the repositioning control is in the activated state and to sale the input distance by a second scaling factor when the repositioning control is in the deactivated state. The first scaling factor is larger than the second scaling factor.

In aspects, the first scaling factor may be in a range of about 100 to about 1000 and the second scaling factor may be in a range of about 1 to about 10. The processing unit may be configured to scale the input distance by dividing the input distance by the first scaling factor when the repositioning control is in the activated state and by dividing the input distance by the second scaling factor when the reposition control is in the deactivated state.

In another aspect of the present disclosure, a method of repositioning an input handle of a robotic surgical system includes detecting movement of an input handle of the robotic surgical system an input distance with a repositioning control of the input handle in a deactivated state, detecting whether a repositioning control of the input handle is in an activated or deactivated state, scaling the input distance to a first output distance or a different second output distance depending on the state of the repositioning control, and actuating movement of a tool supported on an end of a moveable arm of a robotic surgical system the respective scaled first or second output distance.

In aspects, the method includes dividing the input distance by a first scaling factor in a range of 1 to 10 as part of the scaling of the input distance to the first output distance and dividing the input distance by a second scaling factor in a range of 100 to 1000 as part of scaling the input distance to the second output distance. The method may include changing an orientation of the tool as part of the actuating movement when the detected movement of the input handle includes a detected orientation change of the input handle.

In another aspect of the present disclosure, a robotic surgical system including an arm having an end, a tool supported on the end of the arm, an input handle moveable an input distance, an imaging device, and a processing unit. The imaging device is configured to capture images of the tool within a surgical site of a patient. The processing unit is in communication with the input handle. The processing unit is also operatively associated with the arm to move the tool and is in communication with the imaging arm. The processing unit is configured to scale the input distance of the input handle to an output distance based on the position of the imaging device relative to the surgical site of the patient.

In aspects, the system includes an imaging arm with the imaging device positioned at the end of the imaging arm. The input handle may be moveable within a workspace having a center and a limit of movement. The input distance may be defined by the distance between the center and the limit of movement. The imaging device may be configured to zoom out the captured images as the input handle approaches the limit of movement. The processing unit may be operatively associated with the imaging arm and may be configured to move the imaging device away from the surgical site to zoom out the captured images.

In some aspects, the system includes a display that is configured to display the captured images from the imaging device. The processing unit may be configured to scale the input distance to the output distance such that the movement of the tool on the display is substantially equal to the input distance.

In certain aspects, the system includes a switch that is configured to selectively switch the association of the input handle between the tool and the imaging arm. The switch may be a foot switch or disposed on the input handle.

In another aspect of the present disclosure, a method of scaling movement of a tool supported on an end of an arm based on the position of an imaging device relative to a surgical site includes determining the position of the imaging device relative to the surgical site with a processing unit and moving an input handle of a robotic surgical system an input distance to move the tool on output distance. The tool is operatively associated to the input handle by the processing unit. The processing unit scales the input distance to the output distance based on the position of the imaging device relative to the surgical site.

In aspects, moving the input handle includes moving the input handle towards a limit of movement of the input handle. The method may include the processing unit moving the imaging device relative to the surgical site as the input handle approaches the limit of movement. The method may include the processing unit varying a scaling factor as the imaging device is moved relative to the surgical site. The processing unit may scale the input distance to the output distance by the scaling factor.

In another aspect of the present disclosure, a robotic surgical system includes an arm having an end, a tool supported on the end of the arm, an input handle, and a processing unit. The input handle is moveable an input distance in a first input direction and a second input direction opposite the first input direction. The processing unit is in communication with the input handle and is operatively associated with the arm to move the tool. The processing unit is configured to scale the input distance of the input handle to a first output distance of the tool in response to movement of the input handle in the first input direction and to a second output distance of the tool in response to movement of the input handle in the second input direction, the first output distance being different than the second output distance.

In aspects, the processing unit is configured to scale the input distance of the input handle by a first scaling factor in response to movement of the input handle in the first direction and to scale the input distance of the input handle by a second scaling factor in response to movement of the input handle in the second direction. The second scaling factor may be different than the first scaling factor. The processing unit may be configured to scale the input distance by dividing the input distance by one of the first or second scaling factors. The first scaling factor may be in a range of about 1 to about 10 and the second scaling factor may be in a range of about 1 to about 10.

In some aspects, the input handle is moveable within a workspace having a center and a limit of movement. The movement of the input handle in the first direction may be towards the limit of movement and the movement of the input handle in the second direction may be towards the center. The processing unit may be configured to further scale the input distance in response to a location of the input handle between the center and the limit of movement. The processing unit may be configured to linearly or exponentially scale the input distance in response to the location of the input handle between the center and the limit of movement. The processing unit may be configured to increase the first output distance as the location of the input handle is further from the center. The processing unit may be configured to decrease the second output distance as the location of the input handle is further from the center.

In certain aspects, the input handle is configured to scale the input distance of the input handle by a first scaling factor in response to movement of the input handle in the first direction and to scale the input distance of the input handle by a second scaling factor in response to movement of the input handle in the second direction. The second scaling factor may be different than the first scaling factor. The work space may include a first point between the center and the limit of movement with the first and second scaling factor being constant when the input handle is between the center and the first point. One of the first or second scaling factors may vary when the input handle is between the first point and the limit of movement based on the location of the handle.

In another aspect of the present disclosure, a robotic surgical system includes an arm having an end, a tool supported on the end of the arm, and input handle, and a processing unit. The input handle being moveable a first input distance in a first input direction and a second input distance in a second input direction opposite the first input direction, the second input distance being different than the first input distance. The processing unit is in communication with the input handle and operatively associated with the arm to move the tool. The processing unit is configured to move the tool an output distance in a first output direction in response to the first input distance and to move the tool the output distance in a second output direction opposite the first input direction in response to the second input distance.

In yet another aspect of the present disclosure, a method of operation a surgical robot includes moving an input handle of a robotic surgical system an input distance in a first input direction to move a tool supported on an end of an arm of the robotic surgical system a first output distance in response to the movement of the input handle in the first input direction and moving the input handle of the robotic surgical system, the input distance, in a second input direction opposite the first input direction to move the tool a second out distance in response to the movement of the input handle in the second input direction, the second output distance being different than the first output distance.

In aspects, moving the input handle of the robotic surgical system in the first input direction includes moving the input handle towards a limit of movement of a workspace. Moving the input handle of the robotic surgical system in the second input direction may include moving the input handle towards a center of a workspace.

In some aspects, moving the input handle of the robotic surgical system in the first direction includes transmitting an input signal to a processing unit of the robotic surgical system including a location of the input handle relative to a center of a workspace. The method may include the processing unit controlling the first output distance based on the input distance, the first input direction, and the location of the input handle relative to the center of the workspace.

In certain aspects, moving the input handle of the robotic surgical system in the second input direction includes transmitting an input signal to a processing unit of the robotic surgical system including a location of the input handle relative to a center of a workspace. The method may include the processing unit controlling the second output distance based on the input distance, the second input direction, and the location of the input handle relative to the center of the workspace.

In still another aspect of the present disclosure, a method of operating a surgical robot includes moving an input handle of a robotic surgical system a first input distance away from a center of a workspace to move a tool supported on an end of an arm of a surgical robot an output distance in a first output direction and moving the input handle of the robotic surgical system a second input distance towards the center of the workspace to move the tool, the output distance, in a second output direction opposite the first output direction, the second input distance being different than the first input distance.

In other aspects of the present disclosure, the robotic surgical system includes an arm having an end, a tool supported on the end of the arm, an input handle, and a processing unit. The input handle movable an input distance and including a repositioning control having an activated state and a deactivated state. The processing unit may be in communication with the input handle and operatively associated with the arm to move the tool. The processing unit is configured to scale the input distance of the input handle by a first scaling factor when the repositioning control is in the activated state and to scale the input distance by a second scaling factor when the repositioning control is in the deactivated state. The first scaling factor is larger than the second scaling factor.

In aspects, the first scaling factor is in a range of about 100 to about 1000 and the second scaling factor is in a range of about 1 to about 10. The processing unit may be configured to scale the input distance by dividing the input distance by the first scaling factor when the repositioning control in in the activated state and by dividing the input distance by the second scaling factor when the reposition control is in the deactivated state.

In another aspect of the present disclosure, a method of repositioning an input handle of a robotic surgical system includes moving an input handle of a robotic surgical system an input distance with a repositioning control of the input handle in a deactivated state to move a tool supported on an end of an arm of the robotic surgical system a first output distance, and moving the input handle of the robotic surgical system, the input distance, with the repositioning control of the input handle in an activated state to move the tool a second output distance. The input handle being in communication with a processing unit to operatively associate the tool of the robotic surgical system with the input handle. The processing unit scaling the input distance to a first output distance when the input handle is in the deactivated state and scaling the input distance to a second output distance when the input handle is in the activated state.

In aspects, scaling the input distance to the first output distance includes dividing the input distance by a first scaling factor in a range of about 1 to about 10 and scaling the input distance to the second output distance includes dividing the input distance by a second scaling factor in a range of about 100 to about 1000. Moving the input handle the input distance with the repositioning control in the activated state may include an orientation of the input handle operatively associated with an orientation of the tool.

Further details and aspects of exemplary embodiments of the present disclosure are described in more detail below with reference to the appended figures.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Figure 1:
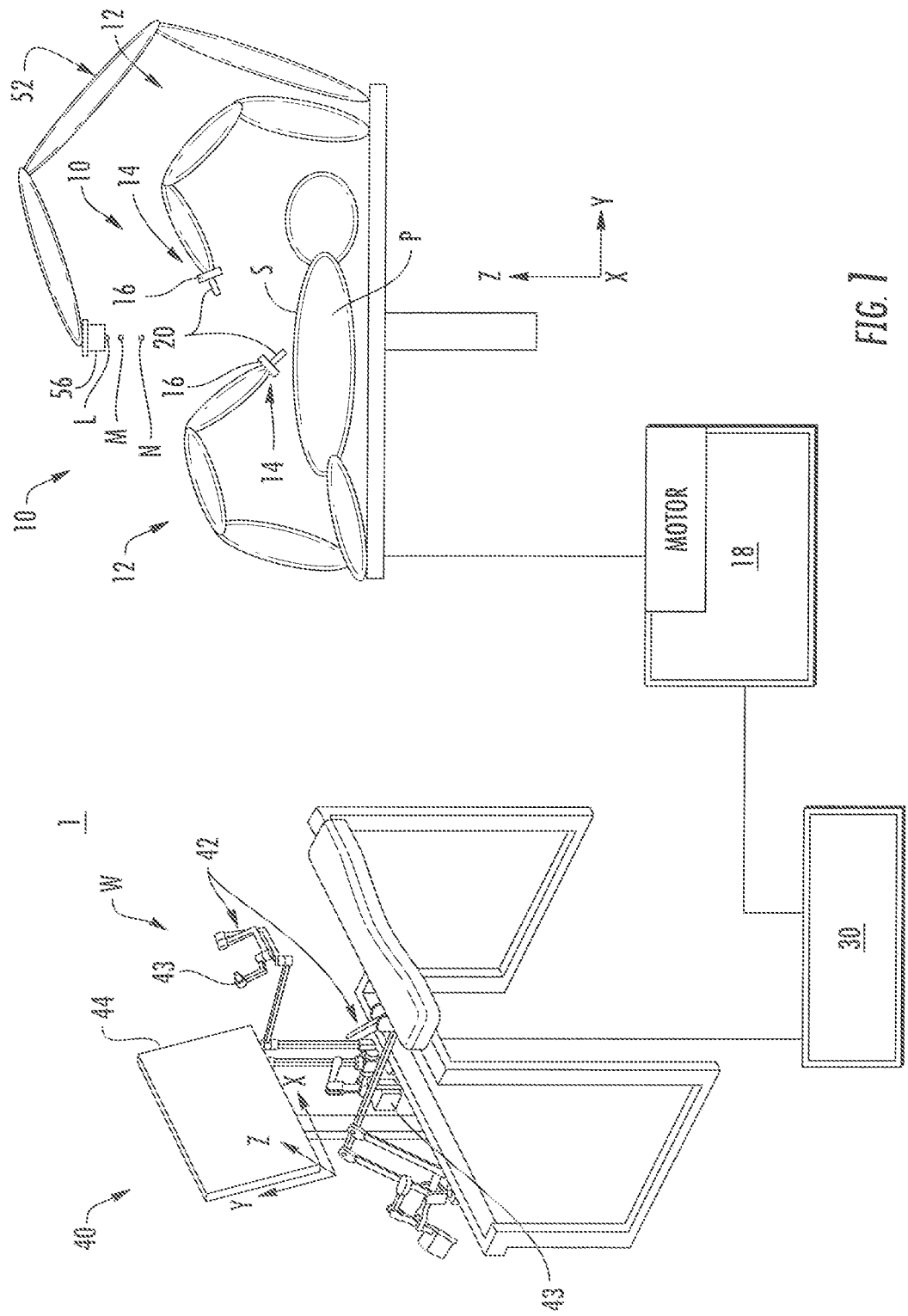
FIG. 1 is a schematic illustration of a user interface and a robotic system in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Referring to FIG. 1, a robotic surgical system 1 in accordance with the present disclosure is shown generally as a robotic system 10, a processing unit 30, and a user interface 40. The robotic system 10 generally includes linkages 12 and a robot base 18. The linkages 12 moveably support an end effector or tool 20 which is configured to act on tissue. The linkages 12 may be in the form of arms each having an end 14 that supports an end effector or tool 20 which is configured to act on tissue. In addition, the ends 14 of the arms 12 may include an imaging device 16 for imaging a surgical site "S". The user interface 40 is in communication with robot base 18 through the processing unit 30.

The user interface 40 includes a display device 44 which is configured to display three-dimensional images. The display device 44 displays three-dimensional images of the surgical site "S" which may include data captured by imaging devices 16 positioned on the ends 14 of the arms 12 and/or include data captured by imaging devices that are positioned about the surgical theater (e.g., an imaging device positioned within the surgical site "S", an imaging device positioned adjacent the patient "P", imaging device 56 positioned at a distal end of an imaging arm 52). The imaging devices (e.g., imaging devices 16, 56) may capture visual images, infra-red images, ultrasound images, X-ray images, thermal images, and/or any other known real-time images of the surgical site "S". The imaging devices transmit captured imaging data to the processing unit 30 which creates three-dimensional images of the surgical site "S" in real-time from the imaging data and transmits the three-dimensional images to the display device 44 for display.

The user interface 40 also includes input handles 42 which allow a clinician to manipulate the robotic system 10 (e.g., move the arms 12, the ends 14 of the arms 12, and/or the tools 20). Each of the input handles 42 is in communication with the processing unit 30 to transmit control signals thereto and to receive feedback signals therefrom. Additionally or alternatively, each of the input handles 42 may include control interfaces (not shown) which allow the surgeon to manipulate (e.g., clamp, grasp, fire, open, close, rotate, thrust, slice, etc.) the tools 20 supported at the ends 14 of the arms 12.

Figure 2:
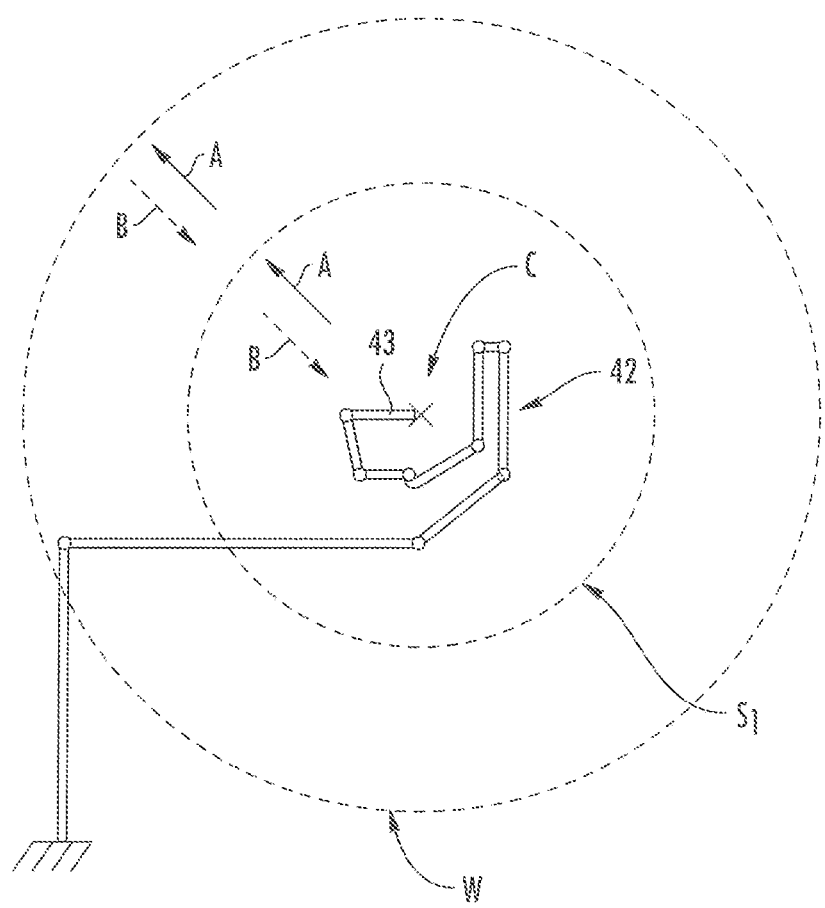
FIG. 2 is a plan view of an arm of the user interface of FIG. 1 within a two-dimensional workspace.

With additional reference to FIG. 2, each of the input handles 42 is moveable through a predefined workspace "W" to move the ends 14 of the arms 12 within a surgical site "S". It will be appreciated that while the workspace "W" is shown in two-dimensions in FIG. 2 that the workspace "W" is a three-dimensional workspace. The three-dimensional images on the display device 44 are orientated such that the movement of the input handle 42 moves the ends 14 of the arms 12 as viewed on the display device 44. It will be appreciated that the orientation of the three-dimensional images on the display device may be mirrored or rotated relative to view from above the patient "P". In addition, it will be appreciated that the size of the three-dimensional images on the display device 44 may be scaled to be larger or smaller than the actual structures of the surgical site permitting the surgeon to have a better view of structures within the surgical site "S". As the input handles 42 are moved, the tools 20 are moved within the surgical site "S" as detailed below. As detailed herein, movement of the tools 20 may also include movement of the ends 14 of the arms 12 which support the tools 20.

For a detailed discussion of the construction and operation of a robotic surgical system 1, reference may be made to U.S. Patent Publication No. 2012/0116416, entitled "Medical Workstation", the entire contents of which are incorporated herein by reference.

The movement of the tools 20 is scaled relative to the movement of the input handles 42. When the input handles 42 are moved within a predefined workspace "W", the input handles 42 send control signals to the processing unit 30. The processing unit 30 analyzes the control signals to move the tools 20 in response to the control signals. The processing unit 30 transmits scaled control signals to the robot base 18 to move the tools 20 in response the movement of the input handles 42. The processing unit 30 scales the control signals by dividing an Input$_{distance}$ (e.g., the distance moved by one of the input handles 42) by a scaling factor $S_F$ to arrive at a scaled Output$_{distance}$ (e.g., the distance that one of the ends 14 is moved). The scaling factor $S_F$ is in a range between about 1 and about 10 (e.g., 3). This scaling is represented by the following equation:

$$\text{Output}_{distance} = \text{Input}_{distance}/S_F.$$

It will be appreciated that the larger the scaling factor $S_F$, the smaller the movement of the tools 20 relative to the movement of the input handles 42.

During a surgical procedure, if the clinician reaches the edge or limit of the predefined range of motion of an input handle 42, the clinician must clutch the input handle 42 (i.e., decouple the motion of the input handle 42 from the motion of the tool 20 of the respective arm 12) to reposition the input handle 42 back within the predefined workspace "W" before continuing to move the input handle 42 in the same direction. As the scaling factor $S_F$ is increased, the clinician may be required to clutch the input handle 42 more frequently, which increases the number of steps and thus, the time and/or costs of the surgical procedure.

In addition, when the input handle 42 is clutched from the tool 20, the orientation (e.g., roll, pitch, and yaw) of the tool 20 is also decoupled from the orientation of the input handle 42. When the input handle 42 is declutched or decoupled, the processing unit 30 may be programmed to align the orientation of the tool 20 with the orientation of the input handle 42, which may result in unintended movement of the tool 20 when the input handle 42 is recoupled. Alternatively, when the input handle 42 is reclutched or recoupled, the processing unit 30 may recalibrate the orientation of the input handle 42 when it is recoupled to the current orientation of the processing unit 30, which may result in the orientation of the input handle 42 being misrepresented by the tool 20.

To reduce or eliminate the need for a clinician to clutch the input handles 42 during a surgical procedure, each of the input handles 42 may include a repositioning control 43 that sends a signal to the processing unit 30 to switch the scaling factor $S_F$ between a procedural scaling factor $PS_F$ and a repositioning scaling factor $RS_F$. The procedural scaling factor $PS_F$ is in a range of about 1.0 to about 10.0 (e.g., 3.0) and the repositioning scaling factor $RS_F$ is significantly larger in a range of about 100.0 to about 1000.0 (e.g., 500.0). The two scaling factors allow a clinician to perform a surgical procedure using the procedural scaling factor $PS_F$ and when one of the input handles 42 approaches an edge or a limit of movement of the predefined workspace "W", the clinician activates the repositioning control 43 to change to the repositioning scaling factor $RS_F$ to move the input handle 42 to a desired position within the predefined workspace "W" without clutching the input handle 42. Once the input handle 42 is at the desired position within the predefined workspace "W", the clinician deactivates the repositioning control 43 to switch back to the procedural scaling factor $PS_F$ to continue the surgical procedure. It will be appreciated that by activating and deactivating the repositioning control 43, to reposition the input handle 42 within the predefined workspace "W", the orientational relationship between the input handle 42 and the end 14 of the arm 12 is maintained. It is contemplated a repositioning control 43 on each input handle 42 is activatable independent of a repositioning control 43 on another input handle 42. While the repositioning control 43 is represented as a button, it is contemplated that the repositioning control 43 may be operated by, but not limited to, a switch, a lever, a trigger, an optical sensor, or a voice command.

Additionally or alternatively, the processing unit 30 may vary the scaling factor $S_F$ based on the direction of movement of the input handle 42 within the predefined workspace "W" to keep the input handle 42 substantially centered within the predefined workspace "W". As detailed below with reference to FIGS. 2-4, a method 300 of varying the scaling factor $S_F$ based on the direction of movement of the input handle 42 is detailed with respect to the "X" axis; however, it will be appreciated that this method 300 may be applied to each of the "X", "Y", and "Z" axes of the predefined workspace "W". When the input handle 42 is moved away from a center "C" (Step 330), of the predefined workspace "W", towards a limit of movement of the predefined workspace "W", the processing unit 30 assigns a first scaling factor $S_{F1}$ to the movement of the input handle 42, records the direction of movement represented by arrow "A", and identifies the limit of movement represented by the border of the workspace "W". When the input handle 42 is moved towards the center "C" of the predefined workspace "W" (Step 335), the processing unit 30 assigns a second scaling factor $S_{F2}$ to the movement of the input handle 42 that is larger than the first scaling factor $S_{F1}$, and records the direction of movement represented by arrow "B". For example, the first scaling factor $S_{F1}$ may be about 3.0 and the second scaling factor $S_{F2}$ may be about 4.5. It is contemplated that first scaling factor $S_{F1}$ may be about 0.70 to about 1.4 times the size of the second scaling factor $S_{F2}$. Varying the scaling factor $S_F$ in this manner keeps the input handle 42 substantially centered by requiring the clinician to move the input handle 42 a greater distance when moving the input handle 42 towards the center "C" of the predefined workspace "W" as compared to the distance that the clinician moved the input handle 42 away from the center "C" to move the tool 20 the same distance in each direction.

Figure 3:
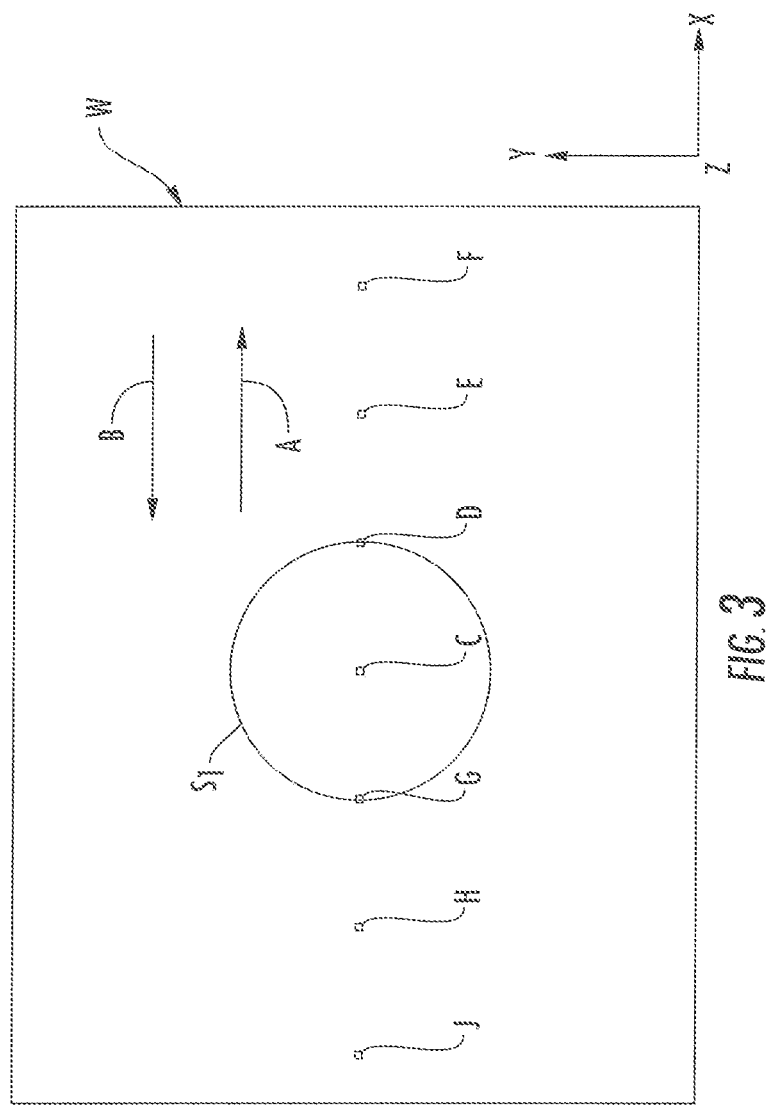
FIG. 3 is a plan view of a workspace of the user interface of FIG. 1.

Accordingly, the center "C" of the predefined workspace "W" continually shifts relative to the surgical site "S" (FIG. 1) during the surgical procedure. It is contemplated that the shifting of the center "C" of the predefined workspace "W" relative to the surgical site "S" may be imperceptible to the clinician. With particular reference to FIG. 3, it will be appreciated that as detailed above, the direction of arrow "A" is representative of the direction of movement of the input handle 42 away from the center "C" towards a point "F"; however, when the input handle 42 is moved from the center "C" towards a point "H", the arrow "B" is representative of movement away from the center "C". In embodiments, the first and second scaling factors $S_{F1}$, $S_{F2}$ are the same in each axis (e.g., the "X", "Y", and "Z" axes). In some embodiments, the first and second scaling factor $S_{F1}$, $S_{F2}$ in one axis (e.g., the "X" axis) is different from the first and second scaling factors $S_{F1}$, $S_{F2}$ in the other axes (e.g., the "Y" and "Z" axes).

Figure 4:
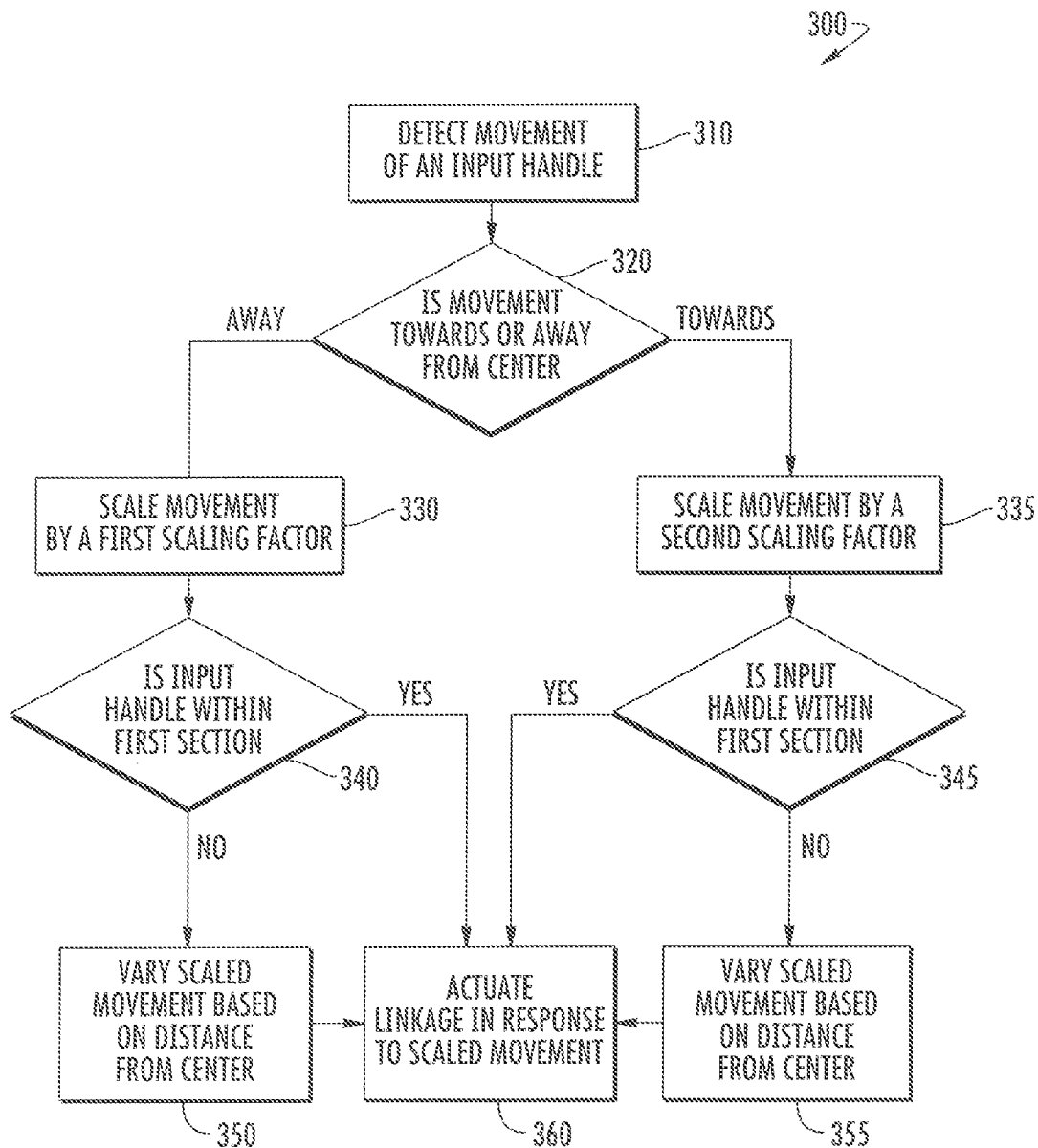
FIG. 4 is a schematic of a method for scaling movement of a user interface in accordance with the present disclosure.

With continued reference to FIGS. 2-4, the method may include the processing unit 30 varying the first and second scaling factors $S_{F1}$, $S_{F2}$ based on the location of the input handle 42 within the predefined workspace "W" (Steps 350, 355). As detailed below, the method of varying a scaling factor $S_F$ based on the location of the input handle 42 is detailed with respect to the "X" axis; however, it will be appreciated that this method may be applied to each of the "X", "Y", and "Z" axes of the predefined workspace "W". Specifically, the scaling factors $S_{F1}$, $S_{F2}$ are implemented by differentiating the movement of the input handle 42 to calculate a handle velocity. This handle velocity is multiplied by the scaling factor (e.g., scaling factors $S_{F1}$, $S_{F2}$). This scaled velocity is then integrated with the current position of the tool 20 to determine a new position of the tool 20 such that movement of the tool 20 is smooth. The scaled velocity is continuously integrated such that the movement of the tool 20 is smooth even if the scaling factor is varied (e.g., when the scaling factor is smoothly or discreetly varied as detailed below).

In accordance with this method and represented as Steps 345 and 355, the second scaling factor $S_{F2}$ may increase as the location of the input handle 42 moves away from the center "C" of the predefined workspace "W" (e.g., the second scaling factor $S_{F2}$ may be larger when the input handle 42 is at point "D" than when the input handle 42 is at center "C", the second scaling factor $S_{F2}$ may be larger when the input handle 42 is at point "E" than when the input handle 42 is at point "D", and the second scaling factor $S_{F2}$ may be larger when the input handle 42 is at point "F" than when the input handle 42 is at point "E"). For example, the second scaling factor $S_{F2}$ may vary in a linear manner based on the location of the input handle 42 from the center "C" such that at point "F" the second scaling factor $S_{F2}$ is about 4.5, at point "E" the second scaling factor $S_{F2}$ is about 4.0, at point "D" the second scaling factor $S_{F2}$ is about 3.5, and at center "C" the second scaling factor $S_{F2}$ is about 3.0.

Alternatively, the second scaling factor $S_{F2}$ may vary as a function of the location of the input handle 42 from the center "C". For example, the second scaling factor $S_{F2}$ may vary in an exponential manner based on the location of the input handle 42 from the center "C" such that at point "F" the second scaling factor $S_{F2}$ is about 6.5, at point "E" the second scaling factor $S_{F2}$ is about 4.5, at point "D" the second scaling factor $S_{F2}$ is about 3.5, and at the center "C" the second scaling factor $S_{F2}$ is about 3.0.

In addition, it is contemplated that the second scaling factor $S_{F2}$ may be constant as the input handle 42 is within a first section Si close to the center "C" and linearly or exponentially increase as the location of the input handle 42 is moved away from the center "C" beyond the first section Si.

It is within the scope of this disclosure that the second scaling factor $S_{F2}$ may increase, in a relatively smooth manner, as the location of the input handle 42 away from the center "C" based on a linear or exponential formula or that the second scaling factor $S_{F2}$ may change discretely at each of a plurality of points (e.g., points "D", "E", and "F") creating discontinuities in the second scaling factor $S_{F2}$.

As detailed above, increasing the second scaling factor $S_{F2}$ requires the clinician to move the input handle 42 a greater distance towards the center "C" when compared to movement of the input handle 42 away from the center "C" to move the tool 20 an equal distance in each direction as the location of the input handle 42 away from the center "C" increases, which shifts the center "C" relative to the surgical site "S" to reduce or eliminate the need to clutch the input handle 42.

In addition as represented in steps 340 and 350, the first scaling factor $S_{F1}$ may decrease as the location of the input handle 42 moves away from the center "C" of the predefined workspace "W" (e.g., the first scaling factor $S_{F1}$ may be smaller when the input handle 42 is at point "D" than when the input handle 42 is at the center "C", the first scaling factor $S_{F1}$ may be smaller when the input handle 42 is at point "E" than when the input handle 42 is at point "D", and the first scaling factor $S_{F1}$ may be smaller when the input handle 42 is at point "F" than when the input handle 42 is at point "E"). For example, the first scaling factor $S_{F1}$ may vary in a linear manner based on the location of the input handle 42 from the center "C" such that at the center "C" the first scaling factor $S_{F1}$ is about 3.0, at point "D" the first scaling factor $S_{F1}$ is about 2.75, at point "E" the first scaling factor $S_{F1}$ is about 2.5, and at point "F" the first scaling factor $S_{F1}$ is about 2.25.

Alternatively, the first scaling factor $S_{F1}$ may vary as a function of the location of the input handle 42 from the center "C". For example, the first scaling factor $S_{F1}$ may vary in an exponential manner based on the location of the input handle 42 from the center "C" such that at the center "C" the first scaling factor $S_{F1}$ is about 3.0, at point "D" the first scaling factor $S_{F1}$ is about 2.75, at point "E" the first scaling factor $S_{F1}$ is about 2.25, and at point "F" the first scaling factor $S_{F1}$ is about 1.25.

In addition, it is contemplated that the first scaling factor $S_{F1}$ may be constant as the input handle 42 is at a location near the center "C" (e.g., when the input handle is between point "D" and a point "G" the first scaling factor $S_{F1}$ is constant) and linearly or exponentially decreased as the location of the input handle 42 is moved beyond point "D" or point "G". It is within the scope of this disclosure that the first scaling factor $S_{F1}$ may increase, in a relatively smooth manner, as the location of the input handle 42 moves away from the center "C" based on a linear or exponential formula or that the first scaling factor $S_{F1}$ may change discretely at each of a plurality of points (e.g., points "D", "E", and "F") creating discontinuities in the first scaling factor $S_{F1}$.

As detailed above, increasing the first scaling factor $S_{F1}$ allows the clinician to move the input handle 42 a lesser distance away from the center "C" as the location of the input handle 42 away from the center "C" is increased to result in the same movement of the tool 20, which in turn shifts the center "C" relative to the surgical site "S" to reduce or eliminate the need to clutch the input handle 42.

It is contemplated that each input handle 42 may vary the respective scaling factors $S_{F1}$, $S_{F2}$ in a similar manner or may vary the respective scaling factors $S_{F1}$, $S_{F2}$ in differing manners (e.g., one input handle 42 may vary its scaling factors $S_{F1}$, $S_{F2}$ based on the location of the input handle 42 and another input handle 42 may vary its scaling factors $S_{F1}$, $S_{F2}$ based on the direction of movement of the another input handle relative to the center "C", each input handle 42 may vary its scaling factors $S_{F1}$, $S_{F2}$ using different linear or exponential formulas). It is also contemplated that an input handle 42 may vary one of the scaling factors $S_{F1}$, $S_{F2}$ and the other of the scaling factors $S_{F1}$, $S_{F2}$ may be constant. While points "F" to "J" are shown spaced evenly apart, it is contemplated that points "F" to "J" may be spaced apart different distances from one another. For example, be spaced closer to one another as the points get closer to the limit of movement.

Referring back to FIG. 1, the robotic surgical system 1 includes an imaging arm 52 that is controlled by the processing unit 30 and may be selectively controlled by the user interface 40. The imaging arm 52 includes an imaging device 56 disposed on a distal end thereof. The imaging device 56 is located over or within the surgical site "S" and is configured to capture the tools 20 acting within the surgical site "S" of the patient "P" and transmit the captured images to the display 44. The imaging device 56 may be a three-dimensional (3D) camera and the display 44 may be a 3D display enabling the clinician to view the surgical site "S" in three dimensions. The imaging device 56 is moveable relative to or within the surgical site "S" in six degrees of freedom and may be selectively moved by one of the input handles 42. The surgical system 1 may include a foot switch (not shown) that switches one of the input handles 42 between a run mode where the input handle 42 is associated with one of the arms 12 to move the tool 20 within the surgical site "S" and a camera mode where the input handle 42 is associated with the imaging arm 52 to move the imaging device 56 about the surgical site "S". It is also contemplated that one of the input handles 42 may include a camera button (not shown) to operatively associate the input handle 42 with the imaging arm 52.

Figure 5:
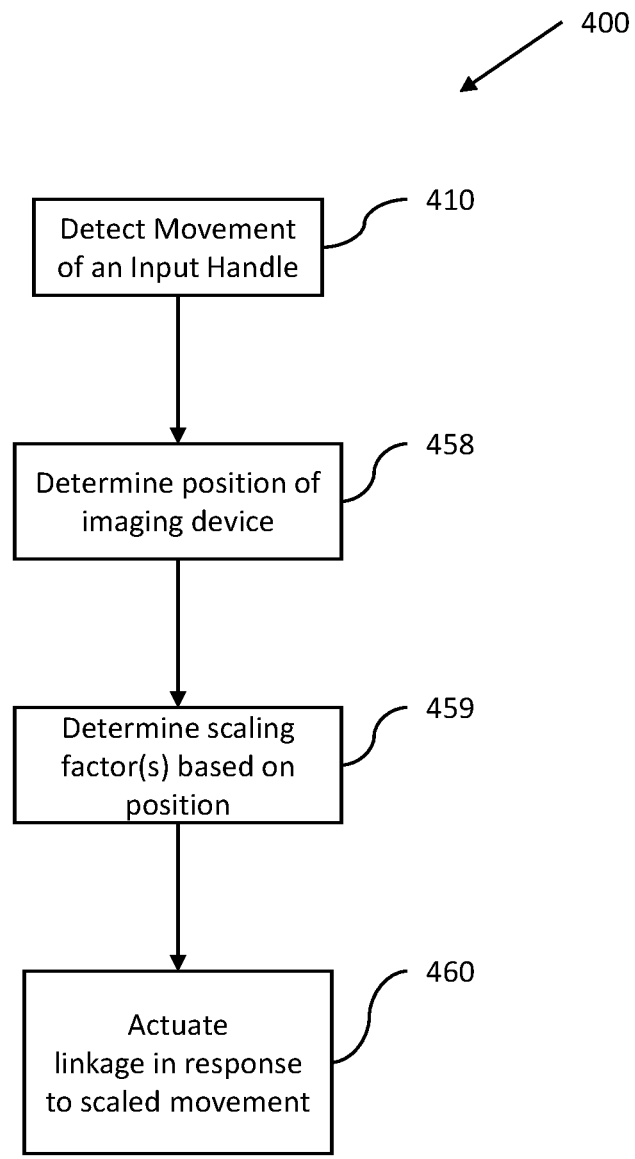
FIG. 5 is a flow chart of a method for scaling movement of a user interface in accordance with the present disclosure.

With reference to the method 400 shown in FIG. 5, the processing unit 30 may determine the location of the imaging device 56 relative to or within the surgical site "S", at step 458, to determine the scaling factor $S_F$, at step 459, used to associate the movement of the input handles 42 detected, at step 410, to the movement of the tools 20 within the surgical site "S", at step 460. As detailed herein, the processing unit 30 determines the location of the imaging device 56 relative to the surgical site "S" along the "Z" axis to determine the scaling factor $S_F$; however, the processing unit 30 may determine the scaling factor $S_F$ based on the location of the imaging device 56 relative to or within the surgical site "S" in each of the "X", "Y", and "Z" axes.

With continued reference to FIG. 1, when the imaging device 56 is in a first position "L" the scaling factor $S_F$ has a first value and when the imaging device 56 is in a second position "M" the scaling factor $S_F$ has a second value larger than the first value. For example, the first value may be about "1" when the imaging device 56 is in the first position "L" and as the imaging device 56 is moved closer to the surgical site "S" to the second position "M", the second value may be about "2", at step 459 of FIG. 5. Continued movement of the imaging device to a third location "N" may further increase the scaling factor $S_F$ to a third value (e.g., about 3), at step 459 of FIG. 5. It will be appreciated that by increasing the scaling factor $S_F$ as the imaging device 56 is moved closer to the surgical site "S", the movement of the tools 20 within the surgical site "S" relative to the movement of the input handles 42 within the predefined workspace "W" is decreased such that the movement of the tools 20 as shown in a field of view on the display 44 is relatively constant for a movement of the input handles 42 within the predefined workspace "W".

The processing unit 30 may be operatively associated with the imaging arm 52 such that as the scaling factor $S_F$ is increased or decreased the processing unit 30 zooms the imaging device 56 in and out from the surgical site "S" to match the movement of the input handles 42 within the predefined workspace "W" to the movement of the tools 20 within the surgical site "S" as viewed by the clinician on the display 44. The zooming in and out of the imaging device 56 may be accomplished by manipulating a lens assembly (not explicitly shown) of the imaging device 56 or by moving the imaging device 56 towards and away from the surgical site "S". The processing unit 30 may zoom the imaging device 56 out when one of the input handles 42 approaches a limit or edge of the predefined workspace "W" to keep the tools 20 within the field of view of the imaging device 56. In addition, the processing unit 30 may reposition the imaging device 56 such that the center "C" (FIG. 2) of the input handles 42 are substantially centered on the display device 44.

It is contemplated that any of the methods of varying the scaling factor $S_F$ or moving of the imaging device 56 may be selectively activated or deactivated by a clinician operating the robotic surgical system 1 before or during a surgical procedure.

It will be appreciated that the scaling factor $S_F$ determined by the processing unit 30 based on the position of the imaging device 56 relative to the surgical site "S" may be varied as detailed above based on the movement of or location of the input handles 42 relative to the center "C" of the predefined workspace "W".

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A method of operating a robotic surgical system, the method comprising:
    detecting a plurality of movements of an input handle of the robotic surgical system;
    determining a location of an imaging device, which is supported by a second linkage of the robotic surgical system, relative to a workspace, which relative location defines a field of view, wherein the field of view represents a movement range of a surgical tool of the robotic surgical system;
    varying a scaling factor for the movement range of the surgical tool within the field of view based on the location of the imaging device, wherein the scaling factor is one of linearly varied or exponentially varied based on the location and a limit of movement of the input handle; and
    scaling a detected movement of the input handle based on the scaling factor.

2. The method of claim 1, further comprising capturing a three-dimensional image using the imaging device.

3. The method of claim 1, further comprising:
    displaying the workspace in three-dimensions.

4. The method of claim 1, wherein varying a scaling factor based on the location of the imaging device includes varying the scaling factor based on an anti-gravity direction with respect to the workspace.

5. The method of claim 1, further comprising:
    switching between a run mode and a camera mode based on a user's selection.

6. The method of claim 5, further comprising:
    moving the imaging device based on the scaled movement of the input handle in the camera mode.

7. The method of claim 5, further comprising:
    moving the surgical tool based on the scaled movement of the input handle in the run mode.

8. A robotic surgical system comprising:
    a first linkage moveably supporting a surgical tool relative to a base and an input handle moveable in a plurality of directions;
    a second linkage moveably supporting an imaging device relative to the base, the imaging device being configured to capture the surgical tool; and
    a processing unit in communication with the input handle operatively associated with the first linkage to move the surgical tool based on a scaled movement of the input handle, and, with the imaging device operatively associated with the second linkage, to move the imaging device,
    wherein the processing unit is configured to:
        determine a location of the imaging device relative to a workspace, which relative location defines a field of view, wherein the field of view represents a movement range of the surgical tool;
        vary a scaling factor for the movement range of the surgical tool within the field of view based on the location of the imaging device, wherein the scaling factor is one of linearly varied or exponentially varied based on the location and a limit of movement of the input handle; and
        scale a movement of the input handle based on the scaling factor.

9. The robotic surgical system of claim 8, wherein the imaging device is a three-dimensional camera.

10. The robotic surgical system of claim 9, further comprising:
a display configured to display the workspace in three-dimensions.

11. The robotic surgical system of claim 8, wherein the imaging device moves in six degrees of freedom.

12. The robotic surgical system of claim 8, wherein the location is based on an anti-gravity direction with respect to the workspace.

13. The robotic surgical system of claim 8, further comprising:
a switch operably connected to the processing unit and configured to switch between a run mode and a camera mode.

14. The robotic surgical system of claim 13, wherein the surgical tool is moved by the input handle in the run mode.

15. The robotic surgical system of claim 13, wherein the imaging device is moved by the input handle in the camera mode.

16. A robotic surgical system comprising:
a first linkage moveably supporting a surgical tool relative to a base and an input handle moveable in a plurality of directions;
a second linkage moveably supporting an imaging device relative to the base, the imaging device being configured to capture the surgical tool; and
a processing unit in communication with the input handle operatively associated with the first linkage to move the surgical tool based on a scaled movement of the input handle, and with the imaging device operatively associated with the second linkage to move the imaging device,
wherein the processing unit is configured to:
determine a location of the imaging device relative to a workspace, which represents a movement range of the surgical tool;
vary a scaling factor based on the location; and
zoom the imaging device in or out from the workspace as the scaling factor is increased decreased.

* * * * *